United States Patent [19]

Tietz

[11] Patent Number: 5,097,005

[45] Date of Patent: Mar. 17, 1992

[54] NOVEL COPOLYESTERS AND THEIR USE IN COMPOSTABLE PRODUCTS SUCH AS DISPOSABLE DIAPERS

[75] Inventor: Raymond F. Tietz, Wilmington, Del.

[73] Assignee: E. I. Du Pont de Nemours and Company, Wilmington, Del.

[21] Appl. No.: 645,995

[22] Filed: Jan. 25, 1991

Related U.S. Application Data

[63] Continuation-in-part of Ser. No. 522,134, May 11, 1990, Pat. No. 5,053,482.

[51] Int. Cl.$^5$ ............................................. C08G 63/20
[52] U.S. Cl. ........................... 528/272; 528/295; 528/301; 528/302; 528/308.6; 525/437; 525/450; 525/471; 428/480
[58] Field of Search ............... 528/272, 295, 301, 302, 528/308.6; 525/437, 450, 471; 428/480

[56] References Cited

U.S. PATENT DOCUMENTS

| | | | |
|---|---|---|---|
| 3,018,272 | 1/1962 | Griffing et al. | 528/293 |
| 3,853,820 | 12/1974 | Vachon | 528/295 |
| 4,418,116 | 11/1983 | Scott | 428/288 |
| 4,483,976 | 11/1984 | Yamamoto et al. | 528/275 |
| 4,526,738 | 7/1985 | Miyoshi et al. | 264/176 |
| 4,704,329 | 11/1987 | Hancock et al. | 428/369 |
| 4,883,706 | 11/1989 | Grosjean | 428/215 |

OTHER PUBLICATIONS

Ingamells, J. Appl. Poly. Sci., vol. 26, 4087–4101 (1981).
Grassie, Developments in Polymer Degradation-5, 112–119 (1984), Applied Science Publishers.

*Primary Examiner*—John Kight, III
*Assistant Examiner*—Sam A. Acquah

[57] ABSTRACT

The invention provides novel copolyesters, fibers and films, nonwovens from the fibers and disposable products of the copolyesters such as diapers. The products are degradable under the conditions typically existing in waste composting processes, have low ingredient costs and yet provide strength and toughness properties adequate for end uses such as in disposable diapers. The copolyesters are based upon polyethylene terephthalate copolymerized with a 5-sulfoisophthalic acid and, if desired, a polyethylene ether, such as diethylene glycol, and include units from hydroxyacids selected for their melting points being lower than their decomposition temperatures.

13 Claims, No Drawings

NOVEL COPOLYESTERS AND THEIR USE IN COMPOSTABLE PRODUCTS SUCH AS DISPOSABLE DIAPERS

CROSS-REFERENCE TO RELATED APPLICATIONS

This Application is a continuation-in-part of my copending parent application Ser. No. 07/522,134, filed May 11, 1990. U.S. Pat. No. 5,053,482.

FIELD OF THE INVENTION

This invention relates to novel copolyesters and products therefrom. The products include fibers, films, nonwovens from the fibers and disposable products such as diapers from such products The products are degradable to innocuous materials under conditions used in municipal solid waste composting systems.

BACKGROUND OF THE INVENTION

The inadequate treatment of municipal solid waste which is being put in landfills and the increasing addition of nondegradable materials, including plastics, to the municipal solid waste streams are combining to reduce drastically the number of landfills available and to increase the costs of municipal solid waste disposal. While the recycling of reusable components of the waste stream is desirable in many instances, there are some products which do not readily fit into this framework, e.g. disposable personal absorbents such as diapers and sanitary napkins, garbage bags, and numerous other products The composting of non-recyclable solid waste is a recognized and growing method of reducing solid waste volume for landfilling and/or making a useful product from the waste to improve the fertility of fields and gardens One of the limitations to marketing such compost is the visible contamination by undegraded plastic such as film and fiber fragments.

As related in my aforesaid parent application, the art was faced with several objectives, as follows:

1 - to provide components which are useful in disposable products and which are degraded into less contaminating forms under the conditions typically existing in waste composting processes. These conditions may involve temperatures no higher than 70° C., and averaging more nearly 55-60° C., humid conditions as high as 100% relative humidity, and exposure times which range from two weeks to more than three months.

2 - to provide disposable components which will not only degrade aerobically in composting, but will continue to degrade in the soil or landfill anaerobically. As long as water is present, they will continue to break down into low molecular weight fragments which can be ultimately biodegraded by microorganisms completely into biogas, biomass and liquid leachate, as for natural organics like wood.

3 - to provide novel polyesters for making the aforementioned fibers, films, coatings and nonwoven sheets of the polyesters, and disposable diapers containing the nonwoven sheets.

4 - to provide polyesters and derivative products which have low ingredient costs and yet provide strength and toughness properties adequate for end uses such as in disposable diapers.

Accordingly, my parent application provided useful novel polyesters consisting essentially of recurring structural units of the formula

—C(O)—R—C(O)—OGO— wherein R is
about 97 to 99.9 mole % para-phenylene (abbreviation T) and
about 0.1 to 3 mole % of a sulfonate radical (abbreviation 5SI)

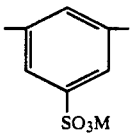

where M is an alkali metal or alkaline earth metal, and wherein G is
about 60 to 80 mole % —$CH_2$—$CH_2$— (abbreviation 2G) and
about 20 to 40 mole % —$(CH_2)_2$—O—$(CH_2)_2$— (abbreviation DEG),
and especially wherein R is about 98 mole % para-phenylene (T) and about 2% of the sulfonate radical (5SI) and G is about 80 mole % —$CH_2$—$CH_2$— (2G) and about 20 mole % —$(CH_2)_2$—O—$(CH_2)_2$—(DEG), and fibers, non-woven sheet, films and combinations thereof, and disposable diapers comprising such materials. Such polyesters are useful for some end uses, e.g., as described in my parent application. For other end uses, however, it would be desirable to provide degradable materials having properties better adapted for such different end uses. In particular, it is sometimes desirable to provide polyesters that can be formed into products that have still further improved rate of hydrolysis, but with similar advantageous properties in many respects, as regards the polyesters that were specifically disclosed by Tietz.

DESCRIPTION OF RELATED ART

Various polyester compositions have been suggested in the past for biodegradable end uses. These include polyhydroxybutyrate, polylactide, polycaprolactone, polyglycolide, and their copolymers. They have not been widely adopted in high volume uses, however, because they are either too expensive or their properties are inadequate for the uses mentioned above.

It is also known to use the salts of 5-sulfoisophthalic acid and its esters as comonomers to improve acid dyeability of polyethylene terephthalate fibers, see for example U.S. Pat. No. 3,018,272 (Griffing et al.). Moreover, this type of fiber is known to have an increased rate of hydrolytic degradation, see for example J. Appl. Poly. Sci., vol. 26, 4087–4094 (W. Ingamells et al.) and Developments in Polymer Degradation 5, edited by N. Grassie, Applied Science Publishers, 1984, pages 112–119. The use of 5-sulfoisophthalate salts together with other neutral comonomers has been disclosed to increase dye rates, but the proportion of the neutral comonomer is usually minimized to affect physical properties as little as possible, see for example U.S. Pat. Nos. 4,704,329 (Hancock et al.) and 3,853,820 (Vachon).

It is also known to use as much as 20 to 45 mole % diethylene glycol as a comonomer with ethylene glycol and terephthalic to provide polyesters having suitable melting and bonding characteristics for a nonwoven binder fiber, see for example U.S. Pat. No. 4,418,116 (Scott).

Further, it is known to prepare water dispersible papermaking binder fibers which are made containing 5 to 20 mole % of diethylene glycol and preferably more than 3 mole % 5-sulfoisophthalate, see for example U.S. Pat. No. 4,483,976 (Yamamoto et al.).

In the latter patent each of the specific polymers disclosed contain 7 mole % or more of the 5-sulfoisophthalate salt.

SUMMARY OF THE INVENTION

The present invention is based on my finding that polyesters such as I describe in my parent application may be advantageously modified by including in the polymer minor proportions of hydroxyacid residues, such as recurring units of polyglycolide, polylactide or polycaprolactone, to increase the rate and ease of hydrolysis of the resulting copolyester, provided care is taken in selection of the particular hydroxyacids, and/or the polyhydroxyacids thereof, so that their decomposition temperature(s) are sufficiently higher than their melting points, and that care is also taken in copolymerising the hydroxyacids and/or their polymers so as not to exceed such decomposition temperatures.

In one embodiment of the invention there is, accordingly, provided a novel fiber and film forming copolyester consisting essentially of about 60-90% by weight recurring structural units(1) of the formula

—C(O)—R—C(O)—OGO— wherein R is about 97 to 99.9 mole % para-phenylene (T) and
about 0.1 to 3 mole % of 5SI sulfonate radical

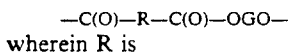

where M is an alkali metal or alkaline earth metal, and wherein G is about 20 to 40 mole % of a polyethylene ether radical —(CH$_2$)$_2$—O—(CH$_2$)$_2$— (abbreviation DEG),
with about 60-80 mole % of ethylene (13(CH$_2$)$_2$— and abbreviation 2G), and
about 2 to 40% by weight of the copolyester being structural units (2) of the formula [—C(O)—Q—O—]$_n$, wherein n is an integer, and wherein Q is such that the hydroxyacid HO—C(O)—Q—OH and/or the polyhydroxyacid HO[—C(O)—Q—O—]$_n$H has a melting point at least 5° C. lower than its decomposition temperature.

Preferably Q may be —CH$_2$—, —CH$_2$—CH$_2$—, —CH$_2$—CH$_2$—CH$_2$—, —C(R')H—, —(CH$_2$)$_5$—, or —C(R')H—CH$_2$— where R' is selected from —CH$_3$, —CH$_2$—CH$_3$, etc.

According to a further aspect of the invention, a process is provided whereby the polyesters may be copolymerized carefully to provide said copolyesters containing, by weight of the copolyester, about 60-98% of (1) the above polyester with about 2 to 40% consisting essentially of structural units (2) of the formula [—C(O)—Q—O—]$_n$, wherein n is an integer, and wherein Q is such that the hydroxy acid HO—C(O)—Q—OH and/or the polyhydroxy acid HO[—C(O)—Q—O—]$_n$H has a melting point at least 5° C. below its decomposition temperature, and Q is as indicated above, wherein the temperature of preparation is carefully controlled so as not to exceed such decomposition temperature.

Other embodiments of the invention include fibers, films and coatings of the above polyesters and nonwovens of the fibers. The invention also contemplates disposable products, such as diapers, which contain an absorbent body portion, with, on at least one surface, a water permeable nonwoven sheet composed of the polyester fibers, a water impermeable film of the polyester, or a combination thereof.

It is a finding of the invention that such polyesters derived from terephthalic acid (abbreviation T), a metal salt of a 5-sulfoisophthalic acid (abbreviation 5SI)), ethylene glycol(abbreviation 2G) and polyethylene ether radical (abbreviations DEG) undergo degradation when subjected to the conditions of high humidity and temperature that typically characterize composting operations, and that the inclusion of hydroxyacid recurring units increases the rate of hydrolysis of these polyesters. It is significant that the bulk of the monomers resulting from degradation, i.e. terephthalic acid, the hydroxyacid and the glycols, are readily digested by organisms in solid waste or compost to create carbon dioxide and water.

A preferred polyester is indicated by the abbreviation (2/98)5SI/T//2G/DEG(80/20), where the numbers connote the mole percentages of the diacid monomeric units in the polyester, with the inclusion of hydroxyacid recurring units. Such abbreviations to connote compositions on a mole % basis will be used throughout this specification.

These provide useful material having applications in end uses where containment of body fluids is necessary and disposability is desirable in a degradable film or a fabric coated with a film which will conform easily to body contours yet act as an effective barrier to penetration of body fluids. It is especially preferred that such a film or coated fabric should have a reduced tendency to rattle and rustle when flexed during body movements. Such a film or fabric must have adequate strength and toughness to allow its survival during use. In order that it not leave objectionable residues when disposed of, it should disintegrate quickly when placed in proper waste disposal facilities and, ultimately, degrade substantially completely to innocuous materials, such as carbon dioxide and water.

Although many copolyesters which are copolymerized with 5-sulfoisophthalic acid (5SI) will hydrolyze readily not all such copolymers are acceptable in the end uses contemplated. The polymers should exhibit the desired physical properties, and be processable under practical conditions, and the products of hydrolysis should desirably have the potential to be digested by the organisms likely to be found in waste disposal facilities and compost. This cannot be achieved by all monomers used in preparing other copolyesters. We have found, for example, that terephthalic acid is decomposed substantially completely in such a test over 28 days, and that ethylene glycol and diethylene glycol radicals are also satisfactorily digested by organisms typical of those found in waste disposal systems; typically, as the molecular weight increases, degradation generally becomes slower. Sodium dimethyl 5-sulfoisophthalate shows very slow degradation in these tests, but it constitutes a

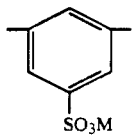

very small proportion of the copolymers of the invention.

DETAILED DESCRIPTION OF PREFERRED EMBODIMENTS

The polyesters consist essentially of recurring structural units of the formula

—C(O)—R—C(O)—OGO— wherein R is about 97 to 99.9 mole % T (para-phenylene) and about 0.1 to 3 mole % of 5SI (i.e., a radical)

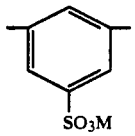

where M is an alkali metal or alkaline earth metal, and wherein G is
about 20 to 40 mole % of a diethylene ether radical —(CH$_2$)$_2$—O—(CH$_2$)$_2$—(DEG),
with about 60 to 80 mole % being ethylene.

These polyesters constitute about 60 to 98% by weight of the copolyesters of the invention, the remaining 2 to 40% by weight of the copolyester being structural units (2) of the formula [—C(O)—Q—O—]$_n$, wherein n is an integer, and wherein Q is such that the hydroxyacid HO—C(O)—Q—OH and/or the polyhydroxyacid HO[—C(O)—Q—O—]$_n$H has a melting point at least 5° C. lower than its decomposition temperature.

Preferably Q may be —CH$_2$—, —CH$_2$—CH$_2$—, —CH$_2$—CH$_2$—CH$_2$—, —C(R')H—, —(CH$_2$)$_5$, or —C(R')H—CH$_2$— where R' is selected from —CH$_3$, —CH$_2$—CH$_3$, etc.

The copolyesters of the invention are water-insoluble, unlike other polyesters which might be derived from the same constituents but which contain very much higher mole percentages of 5SI. They also have relatively low glass transition temperatures, Tg.

Thus advantageously the Tg of the copolyester fibers or films should be no higher than approximately the temperature at which degradation will take place. Since the temperatures in composting operations are often no higher than about 70° C., it is desired that the Tg of the copolyester be no more than about 70° C., preferably about 65° C. or below. Commercial unmodified polyethylene terephthalate (abreviation 2GT) polyester fibers have a Tg of about 80° C. Even a 2GT polyester containing 2.5 mole % of 5SI have a Tg value of 76° C.

It will be understood that with minor variations in composition, it is possible for the copolyesters of the invention to have a further significant reduction in their Tg values. For example, the replacement of up to 5 mole % of the terephthalic acid with an aliphatic acid such as azelaic, succinic, adipic, sebacic or glutaric acid, and the replacement of some of the ethylene glycol with a polyethylene ether, such as DEG or TEG (triethylene glycol) can lower the Tg even below 65° C. Such amounts will not otherwise materially alter the degradation characteristics of the copolyesters, hence their inclusion is contemplated by the term "consisting essentially" used to describe the polyesters and other products of the invention.

Minor amounts of polyfunctional branching agents, such as trimellitic acid residues, may be incorporated to modify melt rheology and film processing, if desired.

The polyesters may be prepared by conventional polycondensation techniques using, for example, as the glycol component, a combination of about 20 to 40 % by weight of the diethylene glycol, with a complemental molecular amount of ethylene glycol, and, as the acid component, a combination of about 97 to 99.9 mole % of terephthalic acid with about 0.1 to 3 mole % of a metal salt of 5-sulfoisophthalic acid. Optionally up to about 5 mole % of the ethylene glycol or terephthalic acid can be replaced, respectively, by another glycol or by an aliphatic acid. In lieu of the mentioned dicarboxylic acids, ester forming derivatives such as the dimethyl esters of the acids may be used.

The glycol component advantageously contains the polyethylene ether radical, such as DEG or TEG, as well as the 2G to achieve an optimum level of degradability without a major sacrifice to fiber and film physical properties such as tensile strength. Above about 40 mole % DEG such properties are adversely affected, as indicated in my parent application.

The acid component is preferably about 1.5 to 2 mole % 5SI. This component is not only relatively costly but also excessively large amounts can render the polyesters water soluble and thus affect the fiber and film physical properties such as shrinkage. As little as 0.1 mole % of the 5SI contributes significantly to the degradability characteristics of the resultant fibers and films.

In the 5SI monomeric units, the metal ion is preferably an alkali metal such as sodium, potassium or lithium. However, alkaline earth metals such as magnesium are also useful. A 5-sulfoisophthalate that has given very good results is the sodium salt.

A relative viscosity of at least 16, preferably at least about 18, is generally acceptable for melt spinning performance.

In the Examples herein, the various monomeric components are charged to a polymerization vessel along with an antimony or other catalyst and subjected to polycondensation conditions to produce a linear polyester in which the units are randomly distributed along the molecular chain. It will be understood that it is also possible, however, to first react two or more of the monomeric components to a prepolymer stage followed by addition of the remaining components which may be polymeric such as polylactide, polyglycolide or polycaprolactone and completion of the polymerization.

The copolyesters of the invention are very hydrolytically sensitive, having a higher equilibrium moisture content than 2GT resin and a faster moisture regain rate. It is desirable that isolated flake be dried thoroughly, preferably to a moisture content below 400 ppm before reextrusion, and to maintain a nitrogen atmosphere around all possible air in leakage points, and to transfer polymer in warm condition (e.g., above about 50° C.) from the dryer to the extruder.

The copolyesters as isolated from the reactor usually have multiple melting points by DSC analysis. These are seen at temperatures which overlap those which might be used in drying 2GT flake, making it difficult to dry these polymers without fusing the flake into a solid mass when they are rapidly heated to get fast economical drying rates. Slower heating to allow crystallization, after which heating at higher temperatures for fast drying, is desirable.

A desirable procedure for preparing high molecular weight resins from rapidly polymerized lower molecular weight ones may be to use solid phase polymerization of low molecular weight flake. This procedure may desirably be carried out after or in combination with the crystallization procedure mentioned above so that temperatures high enough for rapid polymerization can be attained without fusing of the flaked resin. In addition, as known from U.S. Pat. No. 3,544,523, anticaking agents may be useful to prevent sticking, such as Cab-o-sil grade MS-75D, and other finely divided inert solids, like $TiO_2$, talc, carbon black and clay.

If it is desired, for environmental or other reasons, to avoid use of a catalyst that comprises antimony or another heavy metal, then this may be achieved, for instance, by using a crystalline sodium aluminosilicate molecular sieve such as Linde Molecular Sieve 13X, type 9356, with a nominal pore size of 10A, obtained from Union Carbide Corporation. Such procedure is more fully described in commonly assigned U.S. application Serial No. 07/497,069 filed March 20, 1990 in the name of Jackson, but other methods of avoiding antimony may be used, if desired.

In any event, the particular mole percentages of the aforementioned components are desirably selected to provide a polyester which in fiber or film form has a Tg of 70° C. or less, preferably of about 65° C. or less.

As will be understood, while the copolyesters of the invention are well suited for use as fibers or filaments in nonwoven sheets, they can be used to particular advantage in the form of cast and blown films, coatings, or molded articles wherever polyesters with such properties are desired.

Fibers and filaments herein are interchangeable terms in the general sense, but where a more specific acknowledgement of length is appropriate, the term "fibers" is intended to refer to short filaments as in "staple fibers". Hereafter only one of the terms may be used.

The copolyesters of the invention may be converted to fibers or filaments by conventional melt spinning techniques. Deniers of 1 to 15 dpf are most common. The filaments may be used as-spun(undrawn) or in a stretched (drawn or oriented) condition. Drawing to reduce denier or for increasing orientation can be accomplished by the usual procedures.

The polymer compositions of the invention can be formed into nonwoven fabrics via a number of processes. These may be roughly divided into spunbonded fabrics and those fabrics using staple fibers. These are discussed in "Encyclopedia of Textiles, Fibers and Nonwoven Fabrics", Ed. Martin Grayson, John Wiley and Sons, New York, 1984, pp 252-304. The compositions described herein can be used in many such products. Spunbonded nonwovens can be prepared by spinning and laying down simultaneously into webs of continuous filaments using known methods of distributing the threadline in the desired orientation in the web plane. Such webs can be thermally bonded under suitable conditions of time, temperature and pressure to strong fabrics with tensile properties which are usually superior to those obtained with staple webs. Bonding can also be carried out by using suitable adhesives and both these methods may be used to make point bonded or area bonded fabrics. Needle punching may also be used to give the webs stability and strength. Spunbonded fabrics can also be made by melt blowing wherein a stream of molten polymer is extruded into a high velocity stream of heated air and a bonded web formed directly on a screen conveyor from the resultant fibers. Nonwoven fabrics can also be made by direct extrusion through a rotating die into a netlike product (U.S. Pat. No. 3,959,057 J. J. Smith) or by stretching and drawing embossed films of the thermoplastic polymers (British Patent 914,489 and 1,548,865 to Smith and Nephew Research Ltd.).

Staple fibers can be made into nonwovens by several processes. Most of these can be classified into (1) web preparation and (2) reinforcing ("Manual of Nonwovens", Dr. Radko Krcma, Textile Trade Press, Manchester, England, pp 74-76, 1971). During web preparation, bales of staple fiber are opened and formed into a web having either a random orientation (via air, water or electrostatic deposition) or parallel or crosslaid orientation (via carding and plying). Reinforcement to impart physical integrity and useful mechanical properties, can be accomplished by mechanical means such as needlepunching or hydroentanglement (where water jets move fibers out of the plane of the web and entangle them) as in the spunlaced fabrics (U.S. Pat. No. 3,485,706 to Du Pont) or by stitchbonding where a reinforcing thread is sewn through the web. (See "Principles of Stitch Through Technology" Nonwovens Fabrics Forum, Clemson University, Clemson, SC 1978 by J. D. Singelyn). Reinforcement can also be accomplished by adhesive bonding which includes impregnation of the web by a water based resin binder solution or dispersion and subsequent evaporation of the water leaving a fabric which is composed typically of 60-70% by weight fiber and 30-40% by weight binder. Dry adhesive powders may also be applied to the staple web prior to a heating step to produce a powder-bonded nonwoven. Webs of thermoplastic staple fibers may also be reinforced by thermal bonding in which use is made of the ability of the fibers to soften and adhere to each other upon application of heat. As with the spunbonded fabrics these may be point bonded or area bonded. Heat may be applied by hot air (known as through air bonding) or by a pair of patterned and/or flat heated rollers which form a nip through which the web passes to achieve bonding. This process may be carried out with 100% thermoplastic fibers or with blends of thermoplastic fibers with fibers which do not thermally bond in the 100% form, i.e. cotton and rayon.

In addition, nonwoven fabrics can also be made by laminating, extrusion melt coating or adhesively combining the above types of nonwoven fabrics with each other, with films or staple webs in such a way as to confer desired properties on the combined fabric.

In particular, a fabric made by extrusion melt coating a thin, pinhole free film of the compositions of this invention on a nonwoven, made by the spunbonded process or by thermally bonding staple from fibers of this invention alone or in combination with other compostable fibers such as cotton or rayon, is aesthetically pleasing and non-fluid permeable.

The compostable polyester fibers described herein may be used in all these methods of preparing nonwovens to yield fabrics which when subjected to composting conditions will be substantially degraded. Thus staple webs of the polyester fibers, as well as blends of these fibers with cotton and rayon, may be bonded by hydro-entanglement, by needle punching, by wet resin bonding and by dry adhesive bonding. (The adhesives used should be chosen to allow the desired degradation under composting conditions.)

Thermally bonded staple webs of the described compostable polyester fibers can be made in the 100% form or webs containing a significant proportion of these fibers together with cotton and/or rayon may be thermally bonded to fabrics having useful mechanical properties.

Continuous or spun yarns prepared from the compositions described herein may be used to stitch bond webs of fibers such as cotton, rayon or blends of these fibers, or woodpulp, with the compostable polyester fibers of this invention resulting in fabrics which will degrade under composting conditions.

Spunbonded fabrics can be made by thermally bonding webs of continuous fibers prepared from the compostable polyester compositions described herein and by blow spinning, direct extrusion to nets and drawing of embossed films.

The compostable compositions described herein can be melt extruded as films to coat spunlaced nonwoven fabrics which themselves may be composed of compostable fibers alone or in combination with wood pulp, rayon or cotton.

Nonwoven webs of the compostable compositions made by the melt blowing process may also be used as an adhesive layer between other nonwoven fabics.

It is apparent that the fiber, film, and sheet products made from compositions described herein have a great number of applications in products which are disposed of or potentially may be disposed of in composting systems. In addition the compositions have utility in objects made by injection molding, injection blow molding, thermal forming of sheets, rotational molding of powder, extrusion, and pultrusion, which desirably can be disposed of and degraded in composting systems. The following is a nonexclusive list of such end uses:

Agricultural mulch
Agricultural mats containing seeds,
nutrients
Adhesive tape substrate
Baby pants
Bags
Bag closures
Bed sheets
Bottles
Cartons
Disposable diapers
Dust bags
Fabric softener sheets
Garment bags
Garbage and lawn waste bags
Industrial bags
Labels, tags
Monofilaments
Packaging films and structures
Pillow cases
Protective clothing
Surgical drapes
Surgical gowns
Surgical sheets
Surgical sponges
Tampon applicators
Temporary enclosures
Temporary siding
Toys
Wipers The invention can provide fluid impermeable sheets which are compostable in typical waste disposal facilities. Preferably these sheets should not rattle or rustle objectionably and should have strength and toughness adequate for use in personal absorbent products, such as disposable diapers.

The fibers, films and nonwoven fabrics prepared from the compositions of the present invention are of particular utility in disposable diapers since in that use they have an enhanced capability of being degraded in a composting operation. Typical examples of disposable diaper constructions are given in U.S. Pat. Nos. 3,860,003 (Buell) and 4,687,477 (Suzuki et al.), the disclosures of which are incorporated herein by reference. The items which can be made of the compostable compositions of this invention are (1) the backsheet film, i.e. the water-impermeable outside layer, which may be a film which is 100% of the compostable composition or it may be a laminated sheet with a nonwoven or web of compostable fibers including cotton or rayon adhered to the film, (2) the topsheet, i.e. the water-permeable or inner layer, which is a nonwoven fabric of the compostable fiber composition or a blend of the compostable fiber of this invention with cotton or rayon fiber having a porosity suitable for passing urine quickly to the fluid-absorbing pad between the topsheet and backsheet film, and (3) the fastening tapes which may optionally be made from films or nonwovens of the compositions of the invention. The fastening tapes are typically coated with a pressure sensitive adhesive.

It will be apparent that the products of the invention may contain additives such as dyes, pigments, fillers, etc.

TEST METHODS

Polyester glass transition temperatures, Tg, are obtained by using a Du Pont model 2910 Differential Scanning Calorimeter. Samples are heated under a nitrogen atmosphere at a rate of 20° C./min. to a temperature 10°-20° C. above the melting point, then the melt is cooled using the rapid air quench capability of the instrument. The Tg is determined from the second cycle scan done at 20° C./min. using the internal software to determine the inflection point of the baseline shift.

Polymer melting point, m.p., is determined on the first heating cycle as described in Tg determination. The temperature at which the highest endothermic peak occurs is reported as the polymer melting point.

Number average molecular weight, Mn, is determined by gel permeation chromatography (gpc) versus a standard polyethylene terephthalate sample with an Mn of 22000 and a weight average molecular weight of 44000. Polymers are dissolved in and the analysis is run using HFIP containing 0.01M sodium trifluoroacetate as the solvent. A Waters model 150C. ALC/GPC instrument, or its equivalent, is used with two Zorbax PSM-S biomodal columns (sold by E. I. du Pont de Nemours and Company) (or equivalent) in series at 30° C. A refractive index detector was used and data collected at 100 intervals and analyzed via software provided by the instrument supplier.

Carboxyl end groups are determined by titration of an o-cresol solution of the polymer at 115° C. with KOH in benzyl alcohol to a colorimetric endpoint using bromophenol blue as the indicator. Results are reported in eq./106 grams of polymer.

Inherent viscosity is defined in "Preparative Methods of Polymer Chemistry", W. R. Sorenson and T. W. Campbell, 1961, p. 35. It is determined at a concentration of 0.5 g/100 ml of the indicated solvent at the indicated temperature, usually hexafluoroisopropanol (HFIP) at 30° C.

Stress/Strain properties of fibers are given as T/E/M for Tenacity/Elongation/Modulus, in the dimensions of ksi(kilo pounds per square inch) for Tenacity and Modulus, and, as a percentage, Elongation.

Relative viscosity is the ratio of the viscosity of a solution of 0.8 gram of polyester dissolved in 10 ml of hexafluoroisopropanol (HFIP) containing 80 ppm $H_2SO_4$ to the viscosity of $H_2SO_4$-containing HFIP itself, both measured at 25° C. in a capillary viscometer and expressed in the same units.

The "Hydrolysis" results are generally after boiling in water at 100° C., for the indicated period, to show any reductions in molecular weight (Mn), as a percentage, except as indicated, e.g. at 60° C.

This invention will be further illustrated by the following Examples. Parts and percentages are by weight unless otherwise indicated. The 2G/DEG-T/5SI proportions are by mole % of that polymer. The following commercially available materials are used for the indicated hydroxyacid monomer components: (1) the polyglycolide is of inherent viscosity 1.3 dl/g (as measured in hexafluoriosopropanol, HFIP, at 30° C.) and is commercially available as MEDISORB® Bioresorbable Polymer 100 PGA; (2) the polylactide is of intrinsic viscosity 7.93 (as measured in chloroform, $CHCl_3$), and commercially available from CCA Biochem b.v. GORINCHEM, Holland; (3) the polycaprolactone is available from Aldrich 18,160-9).

EXAMPLE 1

This Example shows the preparation of a copolyester of the invention containing about 10% by weight 34 mole % of a polyglycolide, spinning of fibers from this composition, and how readily these fibers can hydrolyse The copolyester is made by mixing the polyglycolide with 2G/DEG(80/20)-T/5SI (98.5/1.5) bearing in mind the fact that there may have been some small deviation in glycol content, as some DEG may have been distilled off during the polymerization.

In a one liter 3-necked flask fitted with a stirrer, $N_2$ inlet and distillation head are placed:

334.8 g ethylene glycol(2G)
0.407 g $Mn(OAc)_2.4H_2O$
0.218 g $Sb_2O_3$
0.278 g NaOAc.

This is heated to 160° C. in an oil bath until all components are dissolved. Then there are added:

63.6 g diethylene glycol(DEG)
571.2 g dimethyl terephthalate(DMT)
14.04 g sodium dimethyl 5-sulfo-isophthalate The temperature of the oil bath is slowly increased. Distillate (methanol) in the amount of 238 ml is collected between 180–220° C. Then 2 ml of a $H_3PO_4$ solution in ethylene glycol is added (4.79 g 85% $H_3PO_4$ diluted to 50 ml with ethylene glycol) and the mixture is stirred for 5 min. The resultant molten monomer is then used to fill a polymer tube about two-thirds full.

Polymerization is continued by attaching a filter flask to the side arm of the polymer tube and inserting a capillary inlet tube drawn finely so as to reach to the bottom of the molten monomer pool. Nitrogen gas is bled in as the tubes are heated in a dimethyl phthalate vapor bath (28C.), first under laboratory vacuum for 1 hour, then at 0.3 mm Hg using a vacuum pump for 6 hours.

The capillary tube is removed from the molten polymer and the polymer is allowed to cool.

The polymer is recovered and ground into small particles in a Thomas mill. The resulting flake is dried at about 130° C. overnight under laboratory vacuum to give the desired 2G/DEG(80/20)-T/5SI(98.5/1.5-)polymer.

50 g of this polymer is mixed with 5.8 g of the indicated polyglycolide in a medium size polymer tube fitted with a drawn-out capillary tube supplied with $N_2$ which reaches to the bottom of the polymer tube. The tube is evacuated and flushed twice with $N_2$ before it is heated to 231° C. in the vapor from a bath of boiling n-decyl alcohol. After the polymers are melted, laboratory vacuum is applied for 15 minutes, then a 0.2 mm Hg vacuum is applied for 2.5 hours while $N_2$ is bubbled through the melt. After cooling, the copolymer is recovered from the broken tube and ground in a Thomas mill. After drying for 48 hrs at 90° C. under laboratory vacuum, the copolymer is molded into a 7/8 inch diameter plug, which is placed in a press spinning apparatus and spun through a 5 hole-(0.015 inch ×0.045 inch) spinneret at 213° C. into fiber that is wound up at 500m/min. The fiber is hand drawn 2× over an 85° C. hot pin. T/E/M is 9 Ksi/116%/214 Ksi. The filaments are about 2 dpf. The carboxyl end group concentration is 183 eq/$10^6$ g.

The Mn (molecular weight) of this fiber was 10,800. After boiling for 2 hours in deionized water, the Mn was reduced to only 5,650. By immersion of the fiber in 60° C. water, the Mn was reduced to 4,575 after 4 weeks; after 8 weeks, it was reduced to 4330.

For comparison, a fiber having a composition of 2G/DEG(80/20)-T/5SI(98/2) and a molecular weight(Mn) of 28,360 had an Mn of 21,100 after 4 weeks in 60° C. water and 18,520 after 8 weeks at 60° C. The copolymer of the present invention was hydrolysed more readily.

EXAMPLE 2

This Example shows the preparation of a copolymer from 90 wt% of 2G/DEG(80/20)-T/5-SI(98.5/1.5) and about 10 wt % (25 mole %) poly L-lactide, its spinning into fibers and hydrolysis of the fibers. The polymer is made and spun similarly to Example 1 except that 5.8 g of the indicated poly L-lactide is used, the polymer is spun at 205 ∝ 210° C. and wound up at 70 m/min. This fiber is drawn 3.5× on an 80° C. hot pin. The fiber had an Mn of 16,100, and a carboxyl end group concentration of 125.5 eq/$10^6$ g. The T/E/M is 26 Ksi/14%/943 Ksi. The filaments are about 8 dpf. After boiling 2 hrs in deionized water, the Mn is 15,900; after 8 hours, it is 11,200; and after 24 hrs, it is 5,230.

EXAMPLE 3

This Example shows the preparation of a copolymer containing 16.4 % by weight (25 mole %) of polycaprolactone with 83.6 wt % of 2G-T/5SI(98/2), and its hydrolysis. A comparison without 5SI was also hydrolysed.

The 2G-T/5SI(98/2) polymer was made essentially as described in Example 1 with;

74.4 g ethylene glycol
0.124 g $Sb_2O_3$
0.100 g $Mn(OAc)_2.4H_2O$ 114.0 g dimethyl terephthalate(DMT)

3.79 g sodium dimethyl 5-sulfo isophthalate

After removal of methanol at temperature up to 225° C., 22.8 g of the polycaprolactone was added and stirring continued for 30 min. The molten product was transferred to a polymer tube, as described in Example 1, and polymerization was continued while the tube was heated with a glycol vapor bath (198° C.) for 1 hour under laboratory vacuum, and then for 5 hours under 0.3mm Hg pressure. The polymer was cooled, ground and dried as in Example 1, then spun using a press spinning apparatus fitted with a 9 mil ×12 mil single hole spinneret at a temperature of 203° C. with a delivery rate of 0.7 cc/min and a windup speed of 38 m/min. The fibers had a Mn of 13,300. Hydrolysis at 100° C. for 8 hrs in deionized water reduced the Mn to 4,500. After 24 hours, the Mn was 3,700.

For comparison, when a similar polymer was made without any 5SI and spun under the same conditions to give a fiber of molecular weight (Mn) 13,550, hydrolysis at 100° C. for 8 hours and even 24 hours hardly reduced the Mn at all, the values being 13,000 and 12,600, respectively.

When a copolymer containing 25 wt % polycaprolactone is made by the same method described above, spun and hydrolyzed in 60 C. water, initial Mn is 10960, after 3 days it is 7510, after 7 days 4400, and after 12 days 3630.

EXAMPLE 4

This Example demonstrates that hydroxyacetic acid can be used in the melt polymerization instead of polyglycolide.

In a 500 ml reaction kettle fitted with a stirrer, $N_2$ inlet and distillation head are placed:

67.0 g ethylene glycol 0.081 g $Mn(OAc)_2 \cdot 4H_2O$ 0.044 g $Sb_2O_3$ 0.056 g NaOAc These are dissolved by heating to 160° C. then 12.7 g diethylene glycol (DEG)

114.2 g dimethyl terephthalate (DMT)

2.80 g sodium dimethyl 5-sulfo isophthalate are added and the solution heated gradually to 220° C. while methanol is distilled off. At this point 19.7 g of hydroxyacetic acid (95% pure) is added and the mixture stirred for 30 minutes.

The molten prepolymer is transferred to a polymer tube as described in Example 1 and polymerization is carried out with the tube immersed in an ethylene glycol vapor bath (198° C.) for 2 hours under laboratory vacuum and 23 hours under about 0.3 mm Hg pressure. The molten polymer forms fibers when the capillary tube is withdrawn.

I claim:

1. A fiber and film forming copolyester consisting essentially of recurring structural units (1) of the formula $$-C(O)-R-C(O)-OGO-$$

in amount about 60-98% by weight,
wherein R is about 97 to 99.9 mole % para-phenylene and about 0.1 to 2.5 mole % of the sulfonate radical

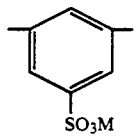

where M is an alkali metal or alkaline earth metal, and
wherein G is
about 60 to 80 mole % $-CH_2-CH_2-$ and
about 20 to 40 mole % $-(CH_2)_2-O-(CH_2)_2-$, and
about 2 to 40% by weight of the copolyester being structural units (2) of the formula $[-C(O)-Q-O-]_n$, wherein n and Q is such that the hydroxyacid $HO-C(O)-Q-OH$ and/or the polyhydroxyacid $HO[-C(O)-Q-O-]_nH$ has a melting point at least 5° C. lower than its decomposition temperature.

2. A copolyester according to claim 1, wherein Q is selected from the group consisting of $-CH_2-$, $-CH_2-CH_2-$, $-CH_2-CH_2-CH_2-$, $-C(R')H-$, $-(CH_2)_5-$, or $-C(R')H-CH_2-$ where R' is selected from $-CH_3$ or $-CH_2-CH_3$.

3. Copolyester according to claim 1 or 2, wherein R is about 98 mole % para-phenylene and about 2% of the sulfonate radical, and G is about 80 mole % $-CH_2-CH_2-$ and about 20 mole % $-(CH_2)_2-O-(CH_2)_2-$.

4. A fiber of the copolyester of claim 1.

5. A fiber of the copolyester of claim 2.

6. A fiber of the copolyester of claim 3.

7. A non-woven sheet of the copolyester of claim 1.

8. A non-woven sheet of the copolyester of claim 2.

9. A non-woven sheet of the copolyester of claim 3.

10. A film of the copolyester of claim 1.

11. A composite of the film of the copolyester of claim 1 and of a layer of nonwoven sheet.

12. A disposable diaper which includes an absorbent body portion having on one surface thereof a water permeable nonwoven sheet of fibers of the polymer of claim 1.

13. A disposable diaper which includes an absorbent body portion having on one surface thereof a water impermeable film of the polymer of claim 1.

* * * * *